United States Patent [19]
Walker et al.

[11] 3,968,136
[45] July 6, 1976

[54] CATALYTIC PROCESS FOR POLYHYDRIC ALCOHOLS AND DERIVATIVES

[75] Inventors: Wellington E. Walker, Charleston; Earle S. Brown, Jr., South Charleston, both of W. Va.

[73] Assignee: Union Carbide Corporation, New York, N.Y.

[22] Filed: July 12, 1974

[21] Appl. No.: 488,140

[52] U.S. Cl. .................. 260/449 L; 252/431 R; 251/431 N; 252/443; 260/485 S; 260/488 J; 260/449.5; 260/449 R
[51] Int. Cl.² .......................................... C07C 27/06
[58] Field of Search .......... 260/449 L, 449.5 449 R; 252/431 R, 431 N, 431 P, 431 L, 443

[56] References Cited
UNITED STATES PATENTS

| 3,081,357 | 3/1963 | Alderson et al. | 252/443 |
| 3,560,539 | 2/1971 | Booth | 252/431 P |
| 3,641,076 | 2/1972 | Booth | 252/431 P |
| 3,833,634 | 9/1974 | Pruett et al. | 260/449 R |

FOREIGN PATENTS OR APPLICATIONS

| 793,086 | 6/1973 | Belgium | 260/449 |

OTHER PUBLICATIONS
Martinengo et al., Gazz., 102 (1972) 344-354.

Primary Examiner—Howard T. Mars
Attorney, Agent, or Firm—George A. Skoler

[57] ABSTRACT

This invention relates to the manufacture of such valuable chemicals as polyhydric alcohols, their ether and ester derivatives, oligomers of such alcohols and monohydric alcohols and their ether and ester derivatives by reacting oxides of carbon and hydrogen in the presence of rhodium carbonyl clusters which possess an infrared spectrum which exhibit three intense wavelength bands between about plus and minus 10 $cm^{-1}$ of about 1868 $cm^{-1}$, about 1838 $cm^{-1}$, and about 1785 $cm^{-1}$ dissolved in a lactone solvent from the group consisting of gamma-butyrolactone and delta-valerolactone.

5 Claims, No Drawings

CATALYTIC PROCESS FOR POLYHYDRIC ALCOHOLS AND DERIVATIVES

This invention is concerned with the manufacture of polyhydric alcohols, their ether and ester derivatives, and oligomers of such alcohols. This invention also produces monohydric alcohols such as methanol, and their ether and ester derivatives.

It is known that monofunctional compounds such as methanol can be obtained by reaction between carbon monoxide and hydrogen at elevated pressures, e.g., up to about 1000 atmospheres, and temperatures ranging from 250°C to 500°C, using mixtures of copper, chromium and zinc oxides as the catalyst therefor. It is disclosed in U.S. Pat. No. 2,451,333 that polyhydroxyl compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British Pat. No. 655,237, published July 11, 1951, there is disclosed the reaction between carbon monoxide and hydrogen at elevated pressures and temperatures, e.g., above 1500 atmospheres at temperatures up to 400°C., using certain hydrogenation catalysts as exemplified by cobalt-containing compounds. U.S. Pat. Nos. 2,534,018; 2,570,792 and 2,636,046 are substantially similar to disclosure to the above said British patent. The only catalysts employed in the numbered examples of said U.S. Pat. No. 2,636,046 are those which contain cobalt.

It is also well-known that nickel is predominantly a catalyst for synthesis and for reforming methane according to the reaction

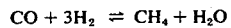

$$CO + 3H_2 \rightleftharpoons CH_4 + H_2O$$

which proceeds from left to right at temperatures below about 500°C. and in the opposite direction at higher temperatures; see Kirk-Othmer, Encyclopedia of Chemical Technology, Second Edition, Volume 4, pages 452–453, John Wiley and Sons, New York (1964).

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making polyhydric aliphatic alcohols, and to their ether, ester and oligomer derivatives. In particular, this invention is concerned with the manufacture of alkane polyols, most specifically, alkane diols and triols, containing 2 or 3 carbon atoms, their ethers, ester and oligomer derivatives. A by-product of this invention is the manufacture of the lesser valuable, but valuable nevertheless, monohydric alkanols such as methanol, ethanol and propanols, and their ether and ester derivatives. The products of the process of this invention contain carbon, hydrogen and oxygen.

This process involves the reaction of oxides of carbon and hydrogen in the presence of a rhodium carbonyl complex provided to the reaction as a rhodium carbonyl cluster which possesses an infrared spectrum which exhibits three intense wavelength bands between about plus and minus 10 $cm^{-1}$ of about 1868 $cm^{-1}$, about 1838 $cm^{-1}$, and about 1785 $cm^{-1}$ at a pressure of at least about 500 pounds per square inch absolute (psia) dissolved in a lactone solvent from the group consisting of gamma-butyrolactone and delta-valerolactone. This means that the rhodium carbonyl cluster exhibits this infrared spectrum either during the reaction or at a temperature and/or pressure below that at which the reaction is effected. In both instances, the catalytic effect is achieved suggesting that the characterized rhodium clusters are always present.

There is described in copending application Ser. No. 462,109, filed Apr. 18, 1974, the process of effecting the aforementioned reaction of oxides of carbon and hydrogen in the presence of a rhodium carbonyl cluster catalyst. One of the difficulties associated with that process is maintaining the stability of the catalyst during the reaction so as to avert catalyst losses. The rhodium is an extremely expensive metal, it currently has a dealer's price of about $715 per troy ounce. Therefore, it is particularly desirable to avoid any loss of any significance of such rhodium values during the course of the reaction.

It has been determined that when the reaction is carried out in the aforementioned lactone solvents, such rhodium losses are significantly reduced. Very few solvents have been found which are comparable to these lactone solvents in minimizing losses of rhodium values in the reaction. Of the two solvents, gamma-butyrolactone is preferred not because of its ability to solvate but because of its lesser ability to polymerize in the reaction to form liquid polyesters therein. Such polyesters are not particularly desirable, yet at the same time do not adversely effect the reaction and the benefits which one accrues from the use of these lactone solvents. It is desirable to conduct the reaction under such conditions so as to minimize such polymerization. It has been found that the polyesters act as adequate solvents for this reaction but they must be periodically removed from the reaction to avoid their build-up in amounts whih would be regarded as deleterious to an efficient operation of the process.

P. Chini, in a review article entitled "The Closed Metal Carbonyl Clusters" published in Reviews (1968), Inorganica Chemica Acta, pages 31–50, states that a metal cluster compound is "a finite group of metal atoms which are held together entirely, mainly, or at least to a significant extent, by bonds directly between the metal atoms even though some non-metal atoms may be associated intimately with the cluster." The rhodium carbonyl cluster compounds of this invention contain rhodium bonded to rhodium or rhodium bonded to another metal, such as cobalt and/or iridium. The preferable rhodium carbonyl cluster compounds of this invention are those which contain rhodium-rhodium bonds. These compounds desirably contain carbon and oxygen in the form of carbonyl (—C—O), in which the carbonyl may be "terminal", "edge bridging" and/or "face bridging". They may also contain hydrogen and carbon in forms other than carbonyl. The following are structures of two rhodium carbonyl cluster ions usable in this invention:

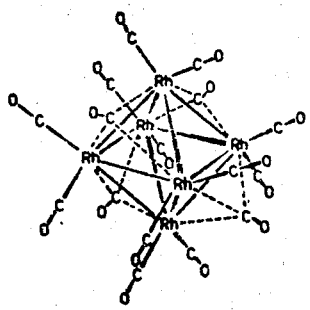

$Rh_6(CO)_{16}$

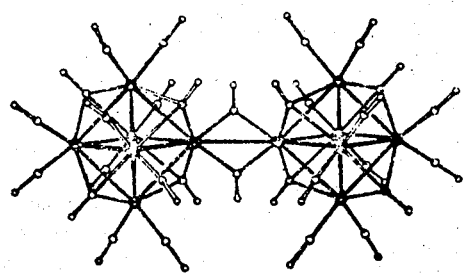

$Rh_{12}(CO)_{30}^{=}$

Rhodium carbonyl cluster ions which possess the infrared spectrum characterized previously, function in association with oxides of carbon and hydrogen, as herein defined, to produce the polyhydric alcohols etc. The exact mechanism by which the cluster compounds act to catalyze the reaction is not fully appreciated at this time. It is believed that the reaction is dependent upon the existance of the following equilibria:

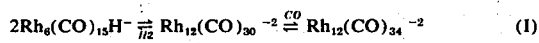

$$2Rh_6(CO)_{15}H^- \rightleftharpoons_{H_2} Rh_{12}(CO)_{30}^{-2} \rightleftharpoons^{CO} Rh_{12}(CO)_{34}^{-2} \quad (I)$$

The clusters of this invention are ionic and they can be associated with any counter-ion provided that conditions are available by which a rhodium carbonyl cluster compound having aforedefined infrared spectrum characteristics is obtainable. The counter-ion may be rhodium per se, hydrogen, ammonia, any monovalent or polyvalent metal, and a broad range of organic compounds, such as those characterized as ligands.

The monovalent or polyvalent metal counter-ion may include lithium, sodium, potassium, rubidium, cesium, francium, beryllium, magnesium, calcium, strontium, barium, radium, scandium, yttrium, the rare earth metals (especially, e.g., cerium, praseodymium, and europium), titanium, zirconium, hafnium, manganese, rhenium, iron, ruthenium, osmium, cobalt, rhodium, iridium, nickel, palladium, platinum, copper, silver, gold, boron, aluminum, gallium, indium and thallium.

The organic counter-ions may result from "complexing" organic compounds with the rhodium carbonyl cluster ions or by ionically associating with the cluster.

The term "complex" means a coordination compound formed by the union of one or more electronically rich molecules or atoms capable of independent existence with one or more electronically poor molecules or atoms, each of which is also capable of independent existence. These organic rhodium cluster complexes are derived from the association of organic ligands with rhodium carbonyl solutions.

Organic ligands which are suitable in the practice of the invention contain at least one nitrogen atom (hereinafter called Lewis base nitrogen atom) and/or at least one oxygen atom (hereinafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium per se a chelate structure. In suitable embodiments the organic ligands contain from 1 and upwards to 4 Lewis base atoms, preferably from 1 to 3 such atoms, and most preferably 1 or 2 Lewis base atoms. These organic ligands are said to be multidentate or polydentate, that is to say, such ligands are bidentate, tridentate, or quadridentate, depending on whether 2, 3, or 4 Lewis base atoms are involved in the formation of chelate structures with rhodium.

Organic ligands which contain at least one Lewis base nitrogen atom will oftentimes hereinafter be referred to as "organic nitrogen ligands; those ligands which contain at least one Lewis Base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino (—N—),
  | nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the

group and the "oxy" oxygen in the

group that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N', N'-tetramethylethylenediamine, N,N,N',N'-tetraethylethylenediamine, N,N,N',N'-tetra-n-propylethylenediamine, N,N,N', N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2-'dipyridyl, ethyl-substituted 2,2'-dipyridyl, 1,4-diazabicyclo [2.2.2] octane, methyl-substituted 1,4-diazabicyclo [2.2.2] octane, purine, 2-aminopyridine, 2-(dimethylamino) pyridine, 1,10-phenanthroline, methyl-substituted 1,10-phenanthroline, 2-(dimethylamino)-6-methoxyquinoline, 7-chloro-1, 10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, digylcolic acid, thiodiglycolic acid, diether ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenezene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N',-tetraacetic acid, the tetramethyl ester of ethylenediaminetetraacetic acid, and the like.

Other organic counter-ions are formed by ionic association with the rhodium carbonyl cluster ions. The are from organic compounds which possess Lewis base nitrogen atoms and typically are composed of carbon, hydrogen and nitrogen. Illustrative of such compounds are, e.g., piperidine, 2-methylpiperidine, 3-methylpiperidine, pyridine, 2-methylpyridine, 4-ethylpiperidine, triethylamine, benzyltrimethyl ammonium acetate and formate, tri-n-butylamine, dibutylamine, methylamine, dodecylamine, morpholine, aniline, benzylamine, octadecylamine, naphthylamine, cyclohexylamine, and the like.

The "oxide of carbon" as covered by the claims and as used herein is intended to mean carbon monoxide and mixtures of carbon dioxide and carbon monoxide, either introduced as such or in situ formed in the reaction.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. No particular advantages at the relatively high concentrations of rhodium are manifest. Depending on various factors such as the counter-ion of choice, the partial pressures of oxides of carbon and hydrogen, the total operative pressure of the system, the operative temperature, the choice of the normally-liquid organic diluent, and other considerations, a catalyst concentration of from about $1 \times 10^{-5}$ to about $1 \times 10^{-1}$ weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100°C. and upwards to approximately 375°C, and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced.

Additionally, one should take notice of the equilibrium reaction for forming ethylene glycol:

$$2\ CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150°C. to about 300°C., and desirably from about 190°C. to about 275°C.

The novel process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. In one embodiment of the invention, the upper pressure limitation is approximately 25,000 psia. Effecting the novel process below about 14,000 psia, especially below about 6,000 psia, results in cost advantages which are associated with low pressure equipment requirements. A suitable pressure range is from about 1000 psia to about 12,000 psia. The pressures referred to above represent the total pressure of hydrogen and oxides of carbon. In a preferred embodiment of the invention, rhodium complex catalyst is maintained in solution in the liquid reaction medium.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mol ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide any hydrogen can also be employed. If desired, the reaction mixture can comprise steam and carbon monoxide.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illlustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reactor. Recovery of the desired product can be achieved by methods well-known in the art such as by distillation, fractionation, extraction, and the like. A fraction comprising rhodium catalyst, generally contained in byproducts and/or normally-liquid organic diluent, can be recycled to the reaction zone, if desired. All or a portion of such fraction can be removed for recovery of the rhodium values or regeneration to the active rhodium species, if necessary. Fresh rhodium catalyst can be intermittently added to the recycle stream or directly to the reaction zone.

Either heterogeneous or homogeneous reaction mixtures may be employed in the practice of the invention. In preferred embodiments, rhodium catalysts as defined herein which are soluble in the reaction medium give outstanding results. However, the synthesis of polyhydric alcohols and/or derivatives thereof can be suitably effected by using such catalysts which are not homogeneously distributed throughout the reaction mixture. Solid catalysts which remain in place during the course of the reaction may be employed. Suspensions of liquid or solid catalysts in liquid and/or gaseous media may be employed. In suitable embodiments of the invention the rhodium catalyst can be used in combination with inert materials or contained or deposited on porous supports such as alumina, silica-alumina, silica gel, activated charcoal, titania, zirconia, zeolites as well as the zeolitic molecular sieves, pumice, kieselguhr, inert porous organic polymers, (e.g., reticulated cation exchange resin) and the like.

The active forms of the rhodium carbonyl clusters may be prepared by various techniques. They can be performed and then introduced into the reaction zone. Alternatively, any of the host of rhodium-containing substances as well as the counter-ion forming substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium(II) propionate, rhodium(II) butyrate, rhodium(II) valerate, rhodium(III) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), tris(hexane-2,4-dionate)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), finely divided rhodium metal, rhodium metal and rhodium-containing compounds deposited on porous supports or carriers such as those exemplified previously, and others.

The preparation of rhodium carbonyl cluster compounds is conveniently carried out in the lactone solvent. Tetrarhodium dodecacarbonyl, though of limited solubility, can be added to the lactone in a finely divided form. Any of several of the rhodium-containing compounds illustrated previously can be employed in lieu of $Rh_4(CO)_{12}$. Organic ligands such as 2-hydroxypyridine or other counter-ion forming compounds can also be added thereto. The cluster forming reaction can be effected under a carbon monoxide pressure, with or without $H_2$, of about 1 to about 15 atmospheres, and higher, using a temperature of about 30°C. to about 100°C., for a period of time ranging from minutes to a few days, generally from about 30 minutes to about 24 hours. The resulting rhodium cluster compound contained in the lactone solvent is catalytically active in this process. The compound contains rhodium in clustered combination with carbon monoxide and the counter-ion of choice. In preparing the aforesaid compounds, one can suitably employ from about .01 to about 20 moles of counter-ion forming compounds per mole of rhodium (contained in the rhodium compound used as a rhodium source). Ratios outside this stated range can be employed especially when it is desirable to use diluent quantities of the counter-ion forming compounds.

The equipment arrangement and procedure which provides the capability for determining the existence of rhodium carbonyl clusters having the aforedefined infrared spectrum characteristics, during the course of the manufacture of polyhydric alcohols from carbon monoxide and hydrogen, pursuant to this invention, is disclosed and schematically depicted in U.S. patent application Ser. No. 462,109, filed Apr. 18, 1974, the disclosure of which is incorporated herein by reference.

A particularly desirable infrared cell construction is described in copending U.S. patent application Ser. No. 451,437, filed Mar. 15, 1974, and its disclosure of a preferred cell construction is incorporated herein by reference.

The oxide of carbon as covered by the claims and as used herein is intended to mean carbon monoxide and mixtures of carbon dioxide and carbon monoxide, either introduced as such or formed in the reaction.

The following examples are merely illustrative and are not presented as a definition of the limits of the invention.

The following procedure represents the procedure and method of analysis used in examples 1 through 11 of Table I.

A 150 ml. capacity stainless steel reactor capable of withstanding pressures up to 7,000 atmospheres was charged with a premix of 75 cubic centimeters (cc) of the specified solvent, 3.0 millimoles (mmol) .77 gms, of rhodium dicarbonylacetylacetonate ($Rh(CO)_2AcAc$), 10 millimoles (mmol) of distilled 2-hydroxypyridine and, where indicated, the specified salt. The reactor was sealed and charged with a gaseous mixture, containing equal molar amounts of carbon monoxide and hydrogen, to the specified pressure measured in pounds per square inch (psig). Heat was applied to the reactor and its contents, when the temperature of the mixture inside the reactor reached 190°C., as measured by a suitably placed thermocouple, an additional adjustment of carbon monoxide and hydrogen ($H_2:CO=1:1$ mole ratio) was made to bring the pressure back to the specified pressure. The temperature was maintained at 220°C. for 4 hours. During this period of time additional carbon monoxide and hydrogen were added whenever the pressure inside dropped about 500 psig below the desired reaction pressure. With these added repressurizations the pressure inside the reactor was maintained at the desired reaction pressure ± 400 psig over the entire 4 hour period.

After the 4 hour period, the vessel and its contents were cooled to room temperature, the excess gas vented and the reaction product mixture was removed. Analysis of the reaction product mixture was made by gas chromatographic analysis using a Hewlitt Packard FM$^{TM}$ 101. The gas chromatograph is held at 50° for 2 minutes after introduction of two microliters of product sample and then programmed from 50° to 280°C. at 15°C. per minute.

The amount of rhodium recovered from the reactor is determined by atomic absorption analysis of the reaction mixture after the four hours of reaction time had lapsed and the unreacted gases were vented to the atmosphere. Atomic absorption analysis was run using a Perkin and Elmer Model 303 Atomic Absorption Spectrophotometer, sold by Perkin and Elmer of Norwalk, Conn., at a slit opening of 0.2 nanometers, a wavelength-setting of 343.5 nanometers, a rhodium hollow cathode lamp as source, operated in the ultraviolet range and using a 100:1 dilution factor of solvent (.08 percent by weight triphenylphosphine in methyl CELLOSOLVE)$^{TM}$ to sample. Rhodium recovered therefore would be the percent of the total rhodium charged that is still soluble or suspended in the reaction mixture at the end of the four hour reaction time.

Another suitable method for measuring the rhodium recovered by atomic absorption analysis is disclosed in an article by Deily, James R., entitled "The Determination of Rhodium in Organic Solutions by Atomic Absorption," appearing in Atomic Absorption Newsletter, 6(3), 65 May–June, 1967.

The rhodium recovered in the wash of the reactor, reported for the examples in Table I was determined by adding to the reactor, which had been emptied after the preceding run, 100cc of the solvent specified in the preceding run, heating the reactor to 160°C and repressurizing with carbon monoxide and hydrogen (CO:H$_2$=60/40) to about 12,000 to about 15,000 psig. The reactor and its contents were maintained at these conditions for 30 minutes then the reactor was cooled to room temperature, depressurized and an analysis of the rhodium recovered in the wash was made by atomic absorption analysis using the same method discussed above.

gamma-butyrolactone and delta-valerolactone at a pressure of from about 500 psig to about 50,000 psig and a temperature of about 100°C. to about 375°C., a mixture consisting essentially of oxides of carbon and hydrogen in the presence of a rhodium carbonyl complex, said complex is provided to the reaction as a rhodium carbonyl cluster which possesses an infrared spectrum which exhibits three intense wavelength bands between about plus and minus 10cm$^{-1}$ of about 1868cm$^{-1}$, about 1838cm$^{-1}$, and about 1785cm$^{-1}$.

2. The process of claim 1 wherein the temperature of the reaction is from about 150°C. to about 300°C.

3. The process of claim 2 wherein the temperature of the reaction is from about 190°C. to about 275°C.

4. The process of claim 1 wherein the pressure of the reaction is from about 1000 psig to about 25,000 psig.

5. The process of claim 4 wherein the pressure of the reaction is from about 1000 psig to about 12,000 psig.

TABLE I

| Example | Solvent[a] | Pressure, psig | Temp. °C | Salt[b] | Glycol gms. | MeOH | Rh Recov. % | Rh in Wash. % |
|---|---|---|---|---|---|---|---|---|
| 1 | γ-B | 10,000 | 220 | — | 1 | 1 | 96 | N.A.[c] |
| 2 | TG | 10,000 | 220 | — | 4 | 1 | 73 | N.A. |
| 3 | γ-B | 8,000 | 220 | Cs-2HP | 2.2 | 2.1 | 93 | 7.0 |
| 4 | TG | 8,000 | 220 | Cs-2HP | 4.1 | 1.7 | 82 | 12.0 |
| 5 | γ-B | 8,000 | 240 | Cs-2HP | 4.5 | 4.1 | 91 | 7.0 |
| 6 | TG | 8,000 | 240 | Cs-2HP | 4.9 | 3.7 | 64 | 13.0 |
| 7 | γ-B | 8,000 | 220 | PPN·OAc | 2.6 | 2.0 | 94 | 7.0 |
| 8 | TG | 8,000 | 220 | PPN·OAc | 3.7 | 1.3 | 81 | |
| 9 | γ-B | 8,000 | 240 | PPN·OAc | 4.8 | 3.8 | 87 | 7.0 |
| 10 | TG | 8,000 | 240 | PPN·OAc | 5.3 | 2.9 | 61 | 17.0 |
| 11 | δ-V | 8,000 | 240 | PPN·OAc | 4.3 | 2.9 | 88 | 5.0 |

[a] γB: γ-butyrolactone; TG: tetraglyme; δ-V: δ-valerolactone.
[b] C$_s$-2HP: cesium 2pyridinolate; PPN·OAc: bis(triphenylphosphine)iminium acetate.
[c] N.A. - No analysis made.

What is claimed is:

1. The process of making alkane polyols which comprises reacting in a solvent selected from the group of

UNITED STATES PATENT OFFICE
CERTIFICATE OF CORRECTION

Patent No. 3,968,136    Dated July 6, 1976

Inventor(s) Wellington E. Walker and Earle S. Brown, Jr.

It is certified that error appears in the above-identified patent and that said Letters Patent are hereby corrected as shown below:

Column 4, line 64:
"(N$^-$=)" should read -- (N$\equiv$) --

Column 6, line 13:
"The" should read -- They --

Column 8, line 4:
"any" should read -- and --

Column 10, line 8:
oxide of carbon" should be in quotes

Signed and Sealed this twenty-third Day of August 1977

[SEAL]

Attest:

RUTH C. MASON
Attesting Officer

C. MARSHALL DANN
Commissioner of Patents and Trademarks